US00PP18014P2

(12) United States Plant Patent

Jonkers et al.

(10) Patent No.: US PP18,014 P2

(45) Date of Patent: Sep. 11, 2007

(54) *IMPATIENS* PLANT NAMED 'SILTE PINKCIE'

(50) Latin Name: *Impatiens walleriana*
Varietal Denomination: Silte Pinkcie

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/410,384

(22) Filed: Apr. 25, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Jondle & Associates P.C.

(57) ABSTRACT

A new *Impatiens* plant particularly distinguished by numerous medium to large, double, deep-pink outer petals and white to light pink inner petals with white centers, medium-green foliage with elliptical leaves, an early flowering response, floriferous throughout the summer, good rain tolerance, a medium-sized, round and bushy plant habit with good branching ability, is disclosed.

1 Drawing Sheet

Genus and species: *Impatiens walleriana.*
Variety denomination: 'Silte Pinkcie'.

BACKGROUND OF THE NEW PLANT

The present invention comprises a new and distinct cultivar of *Impatiens,* botanically known as *Impatiens walleriana,* and hereinafter referred to by the cultivar name 'Silte Pinkcie'. The new cultivar originated from a hybridization made in January 2003 in Andijk, The Netherlands. The female parent was the proprietary white-flowered *Impatiens* plant 'IW-522-1' (unpatented), while the male parent was the proprietary violet-flowered *Impatiens* plant 'IW-68-2' (unpatented). The seeds produced by the hybridization were sown Andijk, The Netherlands in April 2003. A single plant selection was chosen for further evaluation and for asexual propagation in July 2003 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a two-year period. 'Silte Pinkcie' has not been observed under all possible environmental conditions. The present invention has been found to retain its distinctive characteristics through successive asexual propagations.

Plant Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, Netherlands, and Hillscheid, Germany.

1. Numerous medium to large, semi-double, deep-pink flowers with white centers;
2. Medium-green foliage with elliptical leaves;
3. A medium-sized, round and bushy plant habit with good branching ability;

4. An early flowering response;
5. Floriferous throughout the summer; and
6. Good rain tolerance for a double-flowered variety.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is close-up of a portion of a 10-week old plant, grown in a greenhouse in Hillscheid, Germany in late May 2005.

DESCRIPTION OF THE NEW CULTIVAR

The following detailed descriptions set forth the distinctive characteristics of 'Silte Pinkcie'. The data which defines these characteristics were collected from asexual reproductions carried out in Hillscheid, Germany. The plant history was taken in mid September on 9- to 10-week old un-pinched plants which had been planted as rooted cuttings in 12-cm pots in mid-July 2005 and grown in a greenhouse at a minimum temperature of 21° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens walleriana* Hook.
*Common name.*—*Impatiens.*

Parentage:
*Female parent.*—'IW-522-1' a proprietary white-flowered *Impatiens* plant (unpatented).
*Male parent.*—'W-68-2', a proprietary violet-flowered *Impatiens* plant (unpatented).

Growth:

*Growth and plant habit.*—Medium-sized, spreading and mounding growth habit; well-branched; pinching not necessary.

*Height.*—16.8 cm.

*Width.*—15.5 cm.

*Propagation.*—Terminal tips for cuttings.

*Time to produce a finished flowering plant.*—8 weeks for a 12-cm pot.

*Time to initiate and develop roots.*—18 days at less or 22° C.

Branches:

*Average number.*—11.

*Length of main branches.*—13 cm to 17 cm.

*Internode length.*—1.0 cm to 2.0 cm.

*Diameter of branches.*—0.6 cm to 0.8 cm.

*Stem color.*—RHS 145C (light-green), no anthocyanin.

Leaves:

*Arrangement.*—Mainly alternate.

*Size.*—Length: 7.5 cm. Width: 4.2 cm.

*Shape.*—Elliptical.

*Apex.*—Acuminate.

*Base.*—Acute.

*Margin.*—Serrate, ciliate.

*Color* (*mature leaves*).—Upper surface: RHS 137D (medium-green) to RHS 143A (grass-green). Lower surface: RHS 138B to RHS 144B.

*Color* (*immature leaves*).—Near RHS 137C.

*Texture.*—Smooth, glabrous.

*Venation color.*—Upper surface: Indistinct. Lower surface: RHS 145C.

*Petioles.*—Length: 2.5 cm to 3.5 cm. Diameter: 0.3 cm to 0.4 cm. Color: Upper surface: RHS 145D. Lower surface: RHS 145C. Texture: Glabrous.

Flower buds:

*Shape.*—Ovoid to round.

*Size.*—Length: 1.2 cm to 1.3 cm. Diameter: 0.9 cm to 1.0 cm.

*Color at tight bud.*—RHS 68A (pink).

Inflorescence:

*Blooming habit.*—About 6 to 8 weeks after planting of rooted cuttings.

*Inflorescence type.*—Inflorescence appear solitary in the leaf axils of the upper nodes of the stems.

*Number of flowers per inflorescence.*—2 to 4 in various stages of development and emerge at the upper nodes of the stems.

*Flowering season.*—Continuously flowers, mainly from March to October, depending on light intensity.

*Lastingness of the individual blooms on the plant.*—Up to one week (at 18° C. in a greenhouse in the spring).

*Fragrance.*—None.

*Peduncle.*—Color: RHS 144B (light-green). Size: Length: 3.5 cm. Diameter: Up to 0.2 cm. Texture: Flexible, glabrous.

Flowers:

*Form of corolla.*—Semi-double-type.

*Shape of corolla.*—Nearly round outline, outer petals borne more or less parallel to the foliage canopy, while the inner petals are distinctly smaller and directed upright (at right angles to the large petals).

*Corolla size.*—Diameter: 3.9 cm to 4.3 cm. Depth: 1.3 cm.

*Number of petals.*—15 to 18.

Petals:

*Shape.*—Obovate; banner petal is cordate.

*Apex.*—Rounded to slightly retuse.

*Base.*—Attenuate.

*Margin.*—Entire.

*Size.*—Length: 1.8 cm to 2.2 cm. Width: 1.7 cm to 1.8 cm. Banner petal width: 2.4 cm.

*Color.*—General color description: Deep pink with white centers. Upper surface: Outer petals: Initially RHS N66B, then RHS 67C with an RHS 53A (dark-red) macule at the base; RHS 53D (weakly reddish) middle lines that are not always visible. Inner petals: RHS N155B (white) to RHS 69A (pale-pink) in parts. Lower surface: RHS 68B to RHS 68C; RHS N155B for the inner petals.

*Petal texture.*—Smooth, satiny.

*Aspect.*—Outer petals are nearly flat and parallel to the surface of the foliage while the inner petals are more or less directed upright.

Spur:

*Shape.*—Curved, downward directed.

*Color.*—RHS 145C (light-green).

*Size.*—Length: 2.5 cm. Diameter: 0.2 cm at the flower base.

Reproductive organs:

*Stamens.*—Rudimentary fused stamens may appear that are RHS 155A (whitish).

*Style and stigma.*—5, very short, RHS 8D (pale-yellow).

*Ovary.*—5-celled.

Fruit and seed set: No seed set observed.

Disease and insect resistance: No particular resistance or susceptibility has been observed.

COMPARISON WITH PARENTAL AND COMMERCIAL CULTIVARS

'Silte Pinkcie' differs from the female parent 'IW-522-1' (unpatented) by having deep-pink flowers with white centers, while 'IW-522-1' has white flowers.

'Silte Pinkcie' differs from the male parent 'IW-68-2' (unpatented), by having deep-pink flowers with white centers, while 'IW-68-2' has violet flowers.

'Silte Pinkcie' differs from the commercial cultivar 'TiRow' (U.S. Plant Pat. No. 12,467) in that 'Silte Pinkcie' has obovate-shaped outer petals and a cordate-shaped banner petal, while 'TiRow' has exaggerated obovate-shaped petals. 'Silte Pinkcie' has deep-pink outer petals and small white to light-pink inner petals, while 'TiRow' has bi-colored pink flowers. Additionally, 'Silte Pinkcie' has a more compact and smaller plant habit than 'TiRow'.

I claim:

1. A new and distinct cultivar of *Impatiens* plant as shown and described herein.

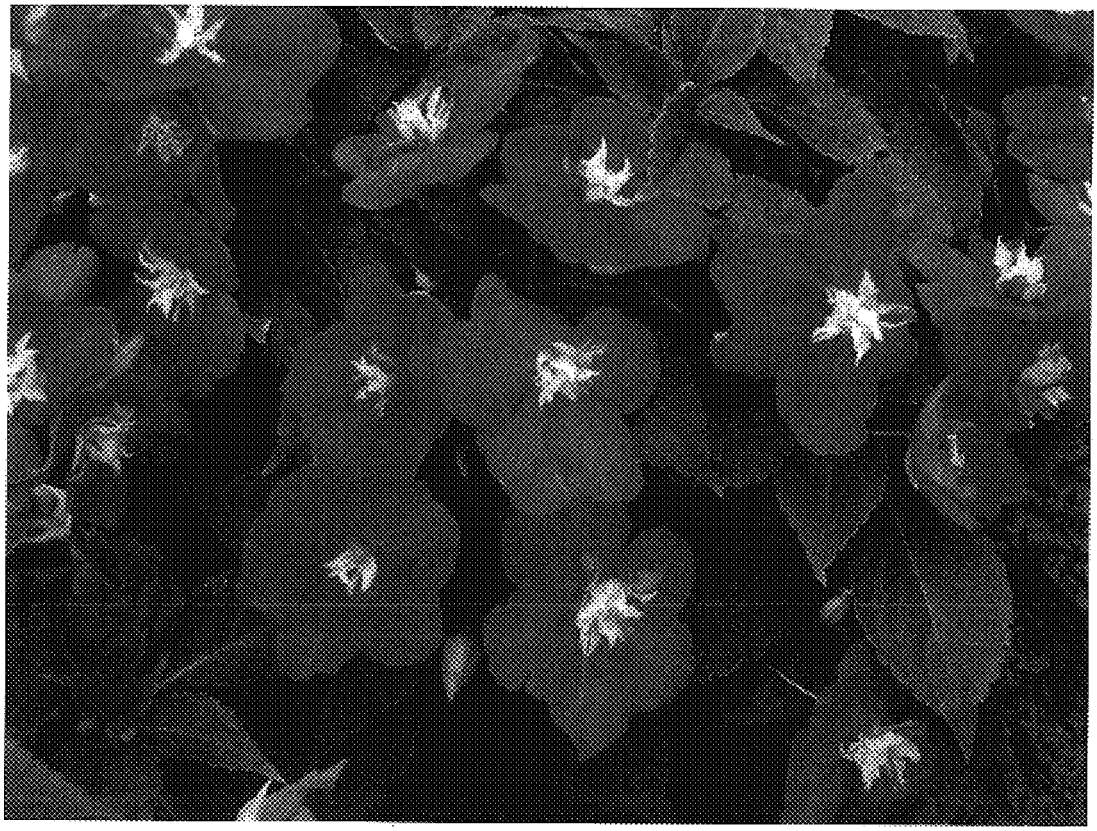

* * * * *